United States Patent [19]

Louderback

[11] 4,126,575

[45] Nov. 21, 1978

[54] BLOOD CONTROL STANDARD

[76] Inventor: Alian L. Louderback, 9661 Longden Ave., Temple City, Calif. 91780

[21] Appl. No.: 853,928

[22] Filed: Nov. 22, 1977

[51] Int. Cl.² ............................................. G01N 33/16
[52] U.S. Cl. .................................. 252/408; 23/230 B; 424/2; 424/3
[58] Field of Search ....................... 23/230 B; 252/408; 424/3, 2

[56] References Cited

U.S. PATENT DOCUMENTS

| | | | |
|---|---|---|---|
| 3,681,255 | 8/1972 | Wilfore | 252/408 |
| 3,859,049 | 1/1975 | Ware et al. | 23/230 B |
| 3,879,510 | 4/1975 | Kitajima et al. | 424/12 |
| 3,973,913 | 8/1976 | Louderback | 23/230 B |
| 3,977,995 | 8/1976 | Louderback et al. | 252/408 |
| 4,001,142 | 1/1977 | Turner | 252/408 |
| 4,027,971 | 6/1977 | Kolman et al. | 23/230 B |

OTHER PUBLICATIONS

Henry, R. J., Clinical Chemistry Principles and Technics, Hoeber Medical Div., Harper & Row, Publ., pp. 731-741, 748-749 (1964).

*Primary Examiner*—Benjamin R. Padgett
*Assistant Examiner*—T. S. Gron

[57] ABSTRACT

A stable blood control standard for the quality control of the measurement of blood pH and gases in the clinical laboratory and method of making the same is disclosed. The blood control standard comprises a sealed receptacle containing specially treated red cells and a gaseous head space at least equal to about the volume of the red cells. The special treatment comprises thoroughly washing and separating the red cells from the plasma components and followed by mildly treating the cells with aldehyde and retaining the cells in a buffered solution. The special treatment also includes treating at least a portion of the red cells with carbon monoxide. The head space comprises from 0–15% $CO_2$, 0–25% $O_2$ and the balance $N_2$ and/or inert gas.

19 Claims, No Drawings

BLOOD CONTROL STANDARD

BACKGROUND OF THE INVENTION

This invention relates to a blood control standard. More particularly, this invention is concerned with a stable blood control standard for the quality control of the measurement of blood pH and gases in the clinical laboratory and method of making the same.

Blood serum is a complex biological fluid containing various components of substantial physiological importance. In the normal or average healthy person the concentrations of these components fall within certain reasonably well-defined limits. When any of these components is found upon analysis to be outside of its normal range, a pathological condition may be indicated which requires medical attention.

The determination of blood gases, electrolytes and the acid-base balance is an important aspect of this blood analysis. Thus, abnormalities in pulmonary function may be indicated by the concentrations of oxygen and carbon dioxide in the blood. The importance of oxygen transport by the blood in respiration and the respiratory regulation of cation-anion balance is well known. By the process of homeostasis, the body tends to preserve a state of equilibrium which is manifested in three ways as applied to water and electrolyte metabolism:

1. Preservation of pH or acid-base balance.
2. Preservation of ionic composition.
3. Preservation of osmolality.

The buffer systems of the intra-and extra-cellular spaces preserve the pH within narrow limits. Of the various physiological buffers, only the bicarbonate system contains a component, carbon dioxide, which is volatile at body temperatures and, therefore, can be regulated by the lungs. Thus, an analysis of the bicarbonate buffer system enables a direct estimation of the respiratory acid-base balance. Dissolved carbon dioxide is present in plasma according to the following equation:

$$CO_2 + H_2O = H_2CO_3 = H^+ + HCO_3-$$

Carbon dioxide also is present in the red cells in the dissolved state, or combined with hemoglobin to form carbamino-$CO_2$, or in a complex based on the action of the enzyme, carbonic anhydrase, which is present in the erythrocytes.

The interrelation between total $CO_2$, bicarbonate, carbonic acid, $pCO_2$ and pH in blood can be shown by the well-known Henderson-Hasselbalch equation:

$$pH = pK + \log \frac{(HCO_3^-)}{(H_2CO_3)}$$

in which
pH is the pH measured in arterial blood
pK is the log of the reciprocal of the dissociation constant of the bicarbonate system
$HCO_3^-$ is the true bicarbonate concentration in mmol/liter.
$H_2CO_3$ is the carbonic acid concentration in mmol/liter The values for pH, total $CO_2$ and $pCO_2$ can be determined experimentally and their mathematical relationships can then be illustrated by application of the Henderson-Hasselbalch equation.

Various instruments have been developed for the determination of the parameters which comprise the blood gases and acid-base balance. These instruments generally are capable of measuring blood pH, $pCO_2$ and $pO_2$. Illustrative of such instruments are those described in U.S. Pat. Nos. 3,658,478 and 3,652,843. Instruments of this type are commercially available from Instrumentation Laboratory Inc. as the IL 113 pH/Blood Gas Analyzer. Another such instrument is the Corning pH/Blood Gas Analyzer described in U.S. Pat. No. 3,763,422. Still another commercially available instrument for measuring blood pH, $pO_2$ and $pCO_2$ is the BMS3 Mk2 Blood Micro System and Digital Acid-Base Analyzer from The London Company, Radiometer A/S Instruments of the latter type are described in U.S. Pat. Nos. 3,654,445 and 3,874,850.

The use of the foregoing and other such instruments for the determination of blood gases in the clinical laboratory presents unique problems of quality control. The instruments must, of course, be properly calibrated in the first instance. Calibration of such instruments can be accomplished by metering standardized gases through the instrument or by application of a calibration fluid such as an aqueous bicarbonate solution as described, for example, in U.S. Pat. No. 3,681,255. However, calibration of the instrument is only one of the problems of blood gas clinical instrumentation. To ensure high quality patient care, the instrumentation system must be tested frequently and laboratory personnel must be promptly responsive to any system malfunction. For the latter purpose, control standards have been developed which can be applied to the instrument periodically at predetermined intervals to ensure adequate quality control. One such type of control standard is a freeze dried human serum which is reconstituted with a liquid diluent prior to use. Examples of this type of control standard are described in U.S. Pat. Nos. 3,466,249 and 3,629,412. These materials, however, are not fully useful for control purposes when the blood gas analysis includes determination of oxygen because the reconstituted serum does not contain the desired level of dissolved oxygen. Rather, they are adapted to control other biological values such as are determined on a Technicon SMA/12 Auto Analyzer.

Another such control standard contains blood which is reconstituted by the addition of a liquid containing fluoride and an iodoacetate or a fluoroacetate to stabilize the blood as disclosed in U.S. Pat. No. 3,859,049. However, this material similarly does not provide the desired levels of oxygen for the control of instruments which include the determination of blood oxygen. Although it is known that blood cells can be stabilized by various chemical fixatives as described in U.S. Pat. Nos. 3,574,137 and 3,640,896 or by thoroughly washing to separate from other blood constituents as described in U.S. Pat. No. 3,558,522, these materials are useful only for blood counting and similar such purposes and do not provide the necessary conditions for the control of blood pH and gases.

It is also known that blood cells can be stabilized for hemagglutination purposes or to serve as affinity absorbents for antigens or antibodies by rigorous treatment of the cells with aldehydes. Such treatment for use in diagnostic tests is described in U.S. Pat. Nos. 3,096,250, 3,426,123, 3,708,572, 3,714,345, and 3,925,541 and U.S. application Ser. No. 362,308, filed May 21, 1973, now U.S. Pat. No. 3,914,400. Again, these materials are useful for the disclosed diagnostic purposes but do not provide the herein-described conditions for control of blood pH and gases.

A recent patent has issued to Allan Louderback, namely, U.S. Pat. No. 3,973,913, the same inventor as herein. The patentee has disclosed a stable blood control standard and method for the quality control of the measurement of blood pH and gases in the clinical laboratory. While the technique includes a sealed receptacle containing specially treated red cells and a gaseous head space at least equal to about the volume of the red cells, no consideration in this prior art has been given to a way to obtain variable carbon monoxide levels with a whole blood product.

If one would just incorporate a quantity of carbon monoxide in the space above the blood in a glass vial, for instance, the results would be variable depending in how long one gassed the vials with carbon monoxide and then followed by gassing with variable oxygen, carbon dioxide and nitrogen in different concentrations as described in the abovementioned patent.

BRIEF SUMMARY OF THE INVENTION

In accordance with the present invention, a stable blood control standard and method is provided for the quality control of the measurement of blood pH and gases in the clinical laboratory. The blood control standard comprises a sealed receptacle containing specially treated red cells and a gaseous head space of at least equal to about the volume of the treated blood cells. This special treatment comprises thoroughly washing and separating of the red cells from the plasma components and mild treatment with aldehyde and retention in a buffered solution. This is accomplished by making red cells 100% saturated with carbon monoxide by long exposure in a stirring solution. Then about five parts of the 100% saturated cells are mixed with 95 parts of normal or subnormal cells to obtain a concentration of cells with about 5% carbon monoxide. The head space consists of a gas or mixture of gases comprising from 0 to 15% $CO_2$, 0 to 25% $O_2$ and the balance substantially $N_2$ and/or inert gas.

The result is a whole blood control designed to verify the analyses of an oximeter instrument which is designed to provide information on one or more of the following assayed constituents.

| Constituents | Also Known As | Reported As |
|---|---|---|
| Total Hemoglobin | Hemoglobin | (g/dl T Ab) |
| Percent Oxyhemoglobin | $O_2$ Saturation | (% $O_2$ Hb) |
| Percent Carboxyhemoglobin | CO Saturation | (% COHb) |
| Oxygen Content | $O_2$ Content | (Vol % $O_2$) |

DEFINITIVE CLINICAL IMPORTANCE OF THE MEASUREMENT OF ABOVE CONSTITUENTS

Hemoglobin — The role of hemoglobin is well documented and is traditionally a measurement of utmost importance in clinical medicine. In the clinical blood gas application, hemoglobin is responsible for carrying gases as oxygen, carbon dioxide and carbon monoxide.

Oxyhemoglobin — A ratio of the amount of hemoglobin combined with oxygen in relation to amount of hemoglobin available for oxygenation.

Carbon Monoxide — Carbon monoxide is not normally present as a metabolic end product in human blood. Environmental exposure can increase the level appreciably. Carbon monoxide is present in smoke and automotive exhaust. City dwellers who are non-smokers have carboxyhemoglobin levels of less than three percent. In heavy smokers, as much as ten percent or more of blood hemoglobin may be combined with carbon monoxide. Carboxyhemoglobin is not an active carrier of blood oxygen. Its poisoning effect of preventing of oxygen binding with hemoglobin is recognized as being much more serious than the loss of a similar amount of hemoglobin by anemia.

Methemoglobin — Methemoglobin is an "inactive" hemoglobin; it is unable to combine reversibly with oxygen and carbon monoxide. It hinders the transfer of oxygen from blood to the tissues with cyanosis occurring at levels of 10–20% Met Hb.

Oxygen Content — The total amount of oxygen in the blood; a summation of oxyhemoglobin and dissolved oxygen.

DETAILED DESCRIPTION OF THE INVENTION

The principal fractions of blood are the plasma, red cells or erythrocytes, platelets and white cells. In the average adult human body which contains about 5 liters of blood, the red cells represent about 2.2 liters. In accordance with the present invention, these red cells are first separated from the other blood components and then treated as defined herein.

In order to prevent clotting in storage, whole blood is normally collected in an anticoagulant solution such as heparin, EDTA ACD or CPD solution. Whole blood collected in this manner can normally be stored for up to 21 to 28 days without seriously affecting the viability of the residual red cells. Since the end of World War II, the collection and storage of blood has undergone considerable change, and various advances in the separation of the blood components have given rise to the practice of modern blood component therapy. By these procedures, the red cells can be separated from whole blood by sedimentation and centrifugation. The separated red cells can be glycerolized and then stored in a frozen state for subsequent use. Similarly, the separated plasma can also be frozen and stored, or its separate plasma can also be frozen and stored, or its separated fractions can be frozen and stored for later use.

In accordance with the present invention, any of the above sources of red cells, fresh or outdated cells (cells stored in excess of 21 to 28 days) can be employed. These cells can be derived from human or other mammalian sources including, for example, equine, bovine, porcine, and sheep species.

In order to ensure complete separation from the other blood components the red cells are sedimented or centrifuged and thoroughly washed. Sedimentation is facilitated by spinning in a conventional blood centrifuge. Centrifuges for such blood cell sedimentation are well-known, and a continuous flow type centrifuge such as is commercially available from the Haemonetics Corp. is preferred. Centrifuges, of this type are described, for example, in U.S. Pat. No. 3,706,412. In this type of centrifuge, the bowl has two parts, one that rotates and another that is stationary. As the blood or previously separated red cells enter the spinning bowl, the cells are distributed to the periphery and as the bowl fills, the supernatant separates from the red cells. The red cells are held in suspension by centrifugal force while the supernatant is expelled through an effluent port into a waste collection receptacle.

A washing solution is then made to follow the same path as the red cells. The washing solution is a saline solution which preferably is normal physiological saline containing about 0.9% NaCl but can also contain other substances such as, for example, the components of Alsever's solution. The geometry of the centrifuge keeps the cells circulating against the flow of fresh wash solution as the used wash solution is expelled through the effluent port. When the washing is complete, the centrifuge is stopped and the washed cells are siphoned into a separate collection vessel.

Another example of a conventional blood centrifuge that is suitable for use in the invention is the Celltrifuge separator which is commercially available from the American Instrument Company.

In the foregoing washing procedures, the red cells are preferably washed with from about 5 to about 30 volumes of the saline washing solution. In a preferred example, a unit of blood (one point) is washed with about 3–4 liters of saline.

Following the saline washing, the red cells are ready for the mild treatment with aldehyde. If not treated immediately, it is preferred to temporarily store the cells in Alsever's solution. This solution can be prepared by admixing the following components in the stated amounts and diluting with water to a volume of three liters.

| Components | Amount |
| --- | --- |
| Glucose (dextrose) | 61.5 grams |
| Sodium Citrate | 24.0 grams |
| Sodium Chloride | 12.6 grams |
| Citric acid (1% solution) | 15.6 ml. |
| Neomycin | 300 mg |
| Chloramphenicol | 990 mg |

The components should be mixed well and the pH adjusted to within a range of about 6.4 to 6.8. The washed red cells can be retained in the Alsever's solution for about 45 days at 2° to 8° C.

The washed red cells, when ready for the aldehyde treatment, are first re-suspended in saline solution in proportions of about one part by volume of cells to about 50 to 30 parts by volume of the saline. The mild treatment with aldehyde which follows comprises the relatively slow addition of a saline solution of the aldehyde to the cells and admixing at room temperature and generally within the range of about 20° to about 26° C. The aldehyde solution preferably ranges from about 0.1 to about 0.6 molar aldehyde in saline. Aldehyde substances which are employed in the aldehyde/saline solution generally are aliphatic aldehydes having from one to about six carbon atoms, such as, for example formaldehyde, acetaldehyde, propionaldehyde, butyraldehyde, malonic aldehyde, succinaldehyde, glutaraldehyde, and pyruvic aldehyde. The saline preferably is normal physiological saline and the aldehyde preferably is a monoaldehyde, especially formaldehyde. The suspension of the red cells in the aldehyde/saline solution is mixed such as by stirring for about 15 minutes to about 4 hours, preferably about 60 minutes, during which time the cells take on a bright red appearance which resembles fresh arterial blood.

Following the mild treatment with aldehyde, the treated cells are sedimented such as by centrifugation and again washed with saline in about the same range of proportions as in the initial saline washing. As before, the red cells can be used directly in the next step or the cells can be temporarily stored in Alsever's solution at 2° to 8° C.

Thereafter, a portion of the red cells in a saline solution are completely saturated with carbon monoxide for a period of 15 to 30 minutes with continuous stirring. After saturation 5 parts of the carbon monoxide saturated red cells are combined with 95 parts of the portion, i.e., untreated with carbon monoxide to produce a 5% carbon monoxide red cell combination. Likewise other concentrations are prepared, i.e., 10 parts of the carbon monoxide saturated red cells with 90 parts of the other unsaturated portion. Also, any number of parts of the carbon monoxide saturated red cell with (100-any) parts of the unsaturated portion.

After completion of the treatment, the red cells are buffered and transferred into suitable receptacles which are capable of being sealed so as to be completely gas tight from the ambient atmosphere. These receptacles can be, for example, glass ampules, vials or bottles.

The buffering of the cells, while not necessary, is such as to maintain a desired pH of from about 6.0 to about 7.7, depending upon whether the blood control standard is to be representative of the normal range, acidosis or alkalosis. Under normal circumstances the normal range is about 7.4±0.1 while the acidosis is 7.0–7.3 and alkalosis is 7.6±0.1. The molarity of the buffer preferably is from about 0.05 to about 0.2 molar. Conventional buffer materials such as, for example, phosphate and tris buffers can be used, but phosphate is generally useful only at a pH of about 7.5. Preferred buffer materials for maintaining the desired pH are N-tris(hydroxymethyl) methyl-2-aminoethanesulfonic acid (TES) and N-2-hydroxyethylpiperazine-N'-2-ethanesulfonic acid (HEPES). These and other such suitable buffer materials are described by Goode et al., Biochemistry, 5, 467–77 (1966).

Sufficient bicarbonate ion, for example, $NaHCO_3$, also is added to the red cells to bring the $pCO_2$ to a level of from about 20 to about 55 mm Hg.

The buffered cells are placed into the receptacles to a level such as to leave a head space at least equal to about the volume of red cells. This head space is then filled with a gas or a mixture of gases comprising 0–15% $CO_2$, 0–25% $O_2$ and the balance $N_2$ and/or inert gas. As used herein, the term inert gas refers to any gas which is inert to the reactions which take place in the electrode systems of the blood pH and gas analyzer instruments. This includes the so-called inert gases which have a completed group of electrons in their outermost shells, for example, He, Ne, Ar, Kr, Xe and Rn. These gases can be added from separate gas sources or as a preadmixture of the desired gases.

The electrodes referred to above are the conventional pH, $pCO_2$ and $pO_2$ electrodes used in the blood pH and gas analysis instruments described hereinbefore. For example, the hydrogen ion concentration may be monitored with a pH responsive glass electrode, in cooperation with a Ag/AgCl reference electrode, the partial pressure of carbon dioxide may be sensed in the circulating fluid by a $CO_2$ electrode and the oxygen may be monitored with an oxygen-sensing electrode.

In order to ensure that the blood control standard will be saturated with the desired gas, the gas preferably is flushed into the receptacle in a volume of from about 10 to about 60 times the volume of the receptacle and the receptacle is then immediately sealed before any significant exchange with atmospheric gas can take place. The desired gas tight sealing can be achieved, for example, by using a glass ampule as the receptacle and melting the top of the ampule in a flame to provide a flame-sealed closure. In the case of vials or bottles, other types of conventional hermetic sealing can be employed.

The gases in the sealed receptacle will then come into equilibrium with the red cells to provide, in essence, a miniature tonometer. This final product remains stable and provides the desired pH, $pO_2$ and $pCO_2$ values for extended periods, for example, up to six months, when stored at about 2° to 8° C. The presence of the red cells also supplies hemoglobin to the blood control standard and, thereby, enables the determination of Base Excess, from which one can calculate $O_2$ content and $O_2$ saturation.

Of course, it is contemplated within the purview of the invention that the cells may be sealed by themselves to be just a control for carbon monoxide and oxygen saturation, which varies i.e., decreases in proportion to the level that the carbon monoxide increases.

The following detailed example will further illustrate the invention although it will be appreciated that the invention is not limited to this specific example.

EXAMPLE

A unit (one pint) of fresh human blood collected in ACD or CPD anticoagulant solution is expressed into a Haemonetics Corp. continuous flow centrifuge. As the blood enters the centrifuge, the red cells are distributed to the periphery and the supernatant is expelled through the effluent port. While spinning, the cells are washed with 3 to 4 liters of a washing solution comprising an aqueous solution of 0.9% NaCl (normal physiological saline). The washed red cells are siphoned into a collection vessel and then transferred to a vessel containing five liters of normal physiological saline. The red cells/saline mixture at 25° C. is then added slowly over a brief time period of 5 to 10 minutes 500 ml of saline containing 40 ml of formaldehyde (37%) solution to thereby provide a 0.1 molar formaldehyde in 0.9% NaCl solution. The mixture is stirred at 25° C. for 60 minutes, during which time the cells assume a bright red color resembling fresh arterial blood. The formaldehyde treated cell mixture is then transferred to the continuous flow centrifuge wherein the cells are further washed with 6 to 8 liters of 0.9% saline solution. The washed cells are then siphoned off into a collection vessel and buffered with an aqueous solution of 0.1 molar HEPES.

A portion of the resultant is then completely saturated with carbon monoxide for a period of 15 to 30 minutes with continuous stirring. Five parts of which saturated material are combined with 95 parts of the unsaturated portion. Also, in a similar manner 10 parts of such saturated material are combined with 90 parts of the saturated parts. Also, any number of parts of the carbon monoxide portion is mixed with (100-any) parts of the concentrated portion to give 5%, 10% and/or any carbon monoxide levels, respectively.

Sufficient $NaHCO_3$ solution is then added to adjust the $pCO_2$ to 40 mm Hg. The pH is given a final adjustment to 7.4. The buffered red cells are then transferred in two ml. aliquots into glass ampules (Wheaton No. 1 glass), each having a capacity of 8 ml. A premixed gas containing 5% $CO_2$, 12% $O_2$ and 83% $N_2$ is then flushed into the ampules at the rate of 600 ml. per 60 seconds, each amplule being flushed with 150 ml. of gas. The ampules are immediately sealed by rotating the top in a flame and pulling off the tip.

The improved blood cell control of the present invention is needed for an Instruments Laboratory Co-oximeter system, i.e., for any instrument measuring carbon monoxide-hemoglobin. What has been disclosed in the foregoing is a way to obtain variable carbon monoxide levels with a whole blood product. If one just put some carbon monoxide in the space above the blood in a glass vial in accordance with the teachings in U.S. Pat. No. 3,973,913, the results would be variable depending on how long one gassed the vials with variable oxygen, carbon dioxide and nitrogen in different concentrations as described in the aforementioned patent. Furthermore, it will be appreciated that carbon monoxide is flammable and cannot be put into a space above the red cells and heat sealed without causing a small burst of flame.

These red cells at any desired concentration of carbon monoxide can be sealed in glass vials or described in U.S. Pat. No. 3,973,913 to obtain a product with variable carbon monoxide, variable oxygen, variable pH and variable carbon dioxide, all independent of each other. Additionally, the blood cells can be increased or decreased to obtain different levels of hemoglobin as described in the aforementioned patent.

Prior to actual use, the resultant improved control standard which had been maintained at 2° C. to 8° C., is treated to eliminate extraneous errors of ambient room temperature and sample handling by incubating at 37° C. for 30 minutes in a water bath to (a) physiologically prepare the sample to that of body temperature, (b) to fully equilibrate the sample with the sealed gases and (c) to prepare the sample to resemble a freshly withdrawn arterial specimen.

Since the measurement of blood gases followed the principles of the natural gas laws temperature is somewhat critical if the sample is to be fully equilibrated to obtain the correct partial pressures. Upon completion of incubation, the ampule is broken and the control sample can be directly aspirated or drawn into a syringe for direct presentation to a blood gas analyzer and/or oximeter instrument.

What is claimed is:

1. A sealed receptacle containing a blood control standard for the quality control of the measurement of blood pH and gases comprising a suspension of treated erythrocytes and a gaseous head space having a volume which is at least equal to about the volume of said erythrocytes, said erythrocytes being treated by thoroughly washing in saline solution, mildly admixing with a solution of aldehyde and saline, thoroughly washing in saline solution, and forming a suspension, at least a portion of the suspension of erythrocytes separately being further treated with carbon monoxide and then combined with a portion of erythrocytes that has been untreated with carbon monoxide, said gaseous head space comprising from about 0% to 15% $CO_2$, from about 0% to about 25% $O_2$, and the balance selected from the group consisting of $N_2$ and inert gases and mixtures thereof.

2. The receptacle containing the blood standard of claim 1 wherein the portion of the suspension of erythrocytes treated with carbon monoxide is treated until the erythrocytes are substantially saturated with the carbon monoxide.

3. The receptacle containing the blood control standard of claim 2 in which the aldehyde is an aliphatic aldehyde having from 1 to about 6 carbon atoms.

4. The receptacle containing the blood control standard of claim 2 in which the aldehyde is formaldehyde.

5. The receptacle containing the blood control standard of claim 2 in which the saline solution is normal physiological saline.

6. The receptacle containing the blood control standard of claim 2 in which the aldehyde concentration is from about 0.1 to 0.6 molar.

7. The receptacle containing the blood control standard of claim 2 in which the mild admixing with aldehyde is performed at about 20° to about 26° C., for about 15 minutes to about 4 hours.

8. The receptacle containing the blood control standard of claim 2 wherein the suspension of treated erythrocytes contains a pH buffer selected from the group consisting of HEPES and TES buffers.

9. A sealed receptacle containing a blood control standard for the quality control of the measurement of blood pH and gases comprising a suspension of treated erythrocytes and a gaseous head space having a volume which is at least equal to about the volume of said erythrocytes, said erythrocytes being treated by thoroughly washing in saline solution, mildly admixing with a solution of aldehyde and saline, thoroughly washing in saline solution forming a suspension thereof, buffering the suspension to a pH of from about 7 to 7.7, combining with a portion of the suspension of erythrocytes separately being further treated with carbon monoxide and then combined with a portion of erythrocytes that has been untreated with carbon monoxide, said combined portions being admixed with bicarbonate ion to a $pCO_2$ of from about 20 to about 55 mm Hg, said gaseous head space comprising from about 0% to about 15% $CO_2$, from about 0% to about 25% $O_2$ and the balance selected from the group consisting of $N_2$ and inert gases and mixtures thereof.

10. The receptacle containing the blood standard of claim 9 wherein the portion of the suspension of erythrocytes treated with carbon monoxide is treated until the erythrocytes are completely saturated with the carbon monoxide and the relative portions of untreated and treated portions are selected whereby the resultant includes 0% to 100% carbon monoxide treated erythrocytes.

11. The receptacle containing the blood control standard of claim 10 in which the aldehyde is an aliphatic aldehyde having from 1 to about 6 carbon atoms.

12. The receptacle containing the blood control standard of claim 9 in which the aldehyde is formaldehyde.

13. The receptacle containing the blood control standard of claim 9 in which the saline solution is normal physiological saline.

14. The receptacle containing the blood control standard of claim 9 in which the aldehyde concentration is from about 0.1 to about 0.6 molar.

15. The receptacle containing the blood control standard of claim 9 in which the mild admixing with aldehyde is performed at about 20° to about 26° C., for about 15 minutes to about 4 hours.

16. The receptacle containing the blood control standard of claim 9 in which the buffer is selected from the group consisting of HEPES and TES buffers.

17. The receptacle containing the blood control standard of claim 16 in which the concentration of the buffer is about 0.05 to about 0.2 molar.

18. The method of making a sealed receptacle containing a blood control standard for the quality control of the measurement of blood pH and gases comprising thoroughly washing erythrocytes in saline solution, mildly admixing with a solution of aldehyde and saline, thoroughly washing in saline solution, forming a suspension, treating at least a portion of the suspension of erythrocytes with carbon monoxide, then combining that portion with a portion of erythrocytes that has been untreated with carbon monoxide, transferring the combined suspension to receptacles while leaving a gaseous head space of at least about equal to volume of said erythrocytes, flushing said head space with a gas comprising from about 0% to about 15% $CO_2$ from about 0% to about 25% $O_2$ and the balance selected from the group consisting of $N_2$ and inert gases and mixtures thereof, and immediately thereafter sealing said receptacles to form a gas tight closure.

19. The method of making a sealed receptacle containing a blood control standard for the quality control of the measurement of blood pH and gases comprising thoroughly washing erythrocytes in saline solution, mildly admixing with a solution of aldehyde and saline, thoroughly washing in saline solution, buffering to a pH of from about 7 to 7.7, forming a suspension, treating at least a portion of the suspension of erythrocytes with carbon monoxide, then combining that portion with a portion of erythrocytes that has been untreated with carbon monoxide, admixing the combined portions with bicarbonate ion to a $pCO_2$ of from about 20 to about 55 mm $H_g$, transferring the combined suspension to a receptacle while leaving a gaseous head space of at least about equal to the volume of said erythrocytes, flushing said head space with a gas comprising from about 0% to about 15% $CO_2$, from about 0% to about 25% $O_2$ and the balance selected from the group consisting of $N_2$ and inert gases and mixtures thereof, and immediately thereafter sealing said receptacles to form a gas tight closure.

* * * * *